(12) United States Patent
Palpu et al.

(10) Patent No.: US 7,186,279 B2
(45) Date of Patent: Mar. 6, 2007

(54) HERBAL DYE AND PROCESS OF PREPARATION THEREOF

(75) Inventors: Pushpangadan Palpu, Uttar Pradesh (IN); Mahesh Pal, Uttar Pradesh (IN); Bhagwan Shankar Dixit, Uttar Pradesh (IN); Ranjan Banerji, Uttar Pradesh (IN); Chandana Venkateswara Rao, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 302 days.

(21) Appl. No.: 11/027,575

(22) Filed: Dec. 30, 2004

(65) Prior Publication Data

US 2006/0143838 A1    Jul. 6, 2006

(51) Int. Cl.
*A61K 7/13* (2006.01)

(52) U.S. Cl. .................. 8/405; 8/425; 8/428; 8/452; 8/460; 8/646

(58) Field of Classification Search .................. 8/405, 8/425, 428, 452, 460, 646
See application file for complete search history.

(56) References Cited

U.S. PATENT DOCUMENTS

2002/0166183 A1* 11/2002 Kaneko .................. 8/550

OTHER PUBLICATIONS

STIC Search Report dated Dec. 14, 2006.*

* cited by examiner

*Primary Examiner*—Eisa Elhilo
(74) *Attorney, Agent, or Firm*—Ladas and Parry LLP

(57) ABSTRACT

The present invention provides a herbal black dye from natural materials comprising of *Juglans regia, Indigofera tinctoria, Terminalia chebula, Acacia accocina, Lawsonia inermis, Trigonella foenum-graecum, Sapindus mukorossi, Eclipta alba, Embelica officinalis, Acacia catechu* and *Piper betle*, the dye derived being safe, non toxic, anti-allergic, anti-dandruff and free from toxic symptoms like itching.

44 Claims, No Drawings

HERBAL DYE AND PROCESS OF PREPARATION THEREOF

FIELD OF THE INVENTION

The present invention relates to herbal dye. More particularly, the present invention relates to a herbal black hair dye and to a process of preparation thereof from natural materials. The mixture of dye derived from the method of present invention can be used in coloring human hair.

BACKGROUND OF THE INVENTION

Synthetic dyes used for coloring of hair have been known for many years. Colorants are classified as being temporary or permanent. In temporary coloring the color can be washed from hair relatively easily. So called permanent coloring of hair typically involves the formulation of aromatic diamine or hydric phenols polycompounds such as para phenylene diamine on the hair fibre. But they are raising so many side effects such as skin cancer, loss or damage of hair, etc. So these synthetic dyes, which are used for coloring hair, are very toxic and thus hazards to human health as well as to the environment.

To color human hair using oxidative dye technology, the hair is generally treated with a mixture of oxidative hair colouring agents and an oxidizing agent. Hhydrogen peroxide is the most commonly used oxidizing agent. However, in addition to oxidizing the oxidative coloring agents, hydrogen peroxide treatment of the hair can also solubilise and decolorize the colored melanin component in the hair, which can lead to undesirable hair qualities, such as brittleness and hair damage.

Over the years significant efforts have been directed towards elimination of many problems associated with the dyeing of human hair. Various approaches to hair dyeing have been developed these includes direct action dyes, natural dyes and oxidative dyes.

Composition of herbal dyes and hair coloring mordants can be used to deliver a variety of hair colors to the hair. However, substantial improvement is needed in the areas of color saturation, color development, precise initial color consistency, improved wash fastness, improved hair condition and level of hair damage.

A brown dye of natural origin can be prepared from the rind of the ripe walnut. Such a dye is described in USSR Certificate no. 1784623 (1992). This dye is often used in food processing industry to stain confectionery products brown so that they resemble chocolate. However, this dye tends to degrade over time. This dye cannot be used in hair because it is unsuitable for cosmetic such as hair color products. A black dye used in food products is derived from drying and refining tealeaves.

Thus, it is desirable to develop a hair coloring composition which exhibits reduced fading, provides improved resistance to wash out during a daily devising regimen, car deliver substantially consistent hair color result throughout the hair, which has reduced irritant effect on skin which has reduced staining on skin and which has reduced adverse effects on the hair of the user. It is also desirable to develop a convenient, eco-friendly and easy to use method for the delivery of such a hair coloring formulation to the hair.

There is also a need for natural hair coloring composition which effectively dye the hair but avoid or reduce damage to the hair which can color the hair effectively and avoid reduce irritation and or staining to the skin of the user.

There is a need for black dye produced from natural materials that may be used in wide variety of context including hair color products. There is additional need for a method of producing such a dye in high yield manner.

OBJECT OF THE INVENTION

The primary objective of the invention is to prepare herbal black dye for coloring hair, which prevents damage hair, skin irritation and reduced staining of skin, remove dandruff and conditions hair.

Another object of the invention is to prepare a composition that has no side effect.

Another objective of the invention is to prepare herbal composition with a combination of the plants, which are rich source of tannins and can be used in skin disease.

It is another object of the invention to provide a single pack fast acting hair-coloring composition, which is simple to use.

SUMMARY OF THE INVENTION

The present invention provides a herbal dye composition comprising a mixture of:
(a) dyes extracted from plants *Juglans regia, Indigofera tinctoria, Terminalia chebula, Acacia sinuata, Lawsonia inermis, Trigonella foenum-graecum, Sapindus mukorossi Eclipta alba, Embelica officinalis, Acacia catechu* and *Piper betle,*
(b) and a hair coloring mordant, In one embodiment of the invention, the pH of each of (a) and (b) is in the range of 2 to 5.

In another embodiment of the invention, the mixture of (a) and (b) has a pH in range of 2 to 5.

It is to be understood that the percentage weight of the composition dye components herein are expressed in terms of the total composition.

In another embodiment of the invention, component (a) comprises on a wt/wt % of the total composition, a dye of *Juglans regia* 20–30%, a dye of *Indigofera tinctoria* 10–20%, a dye of *Acacia sinuata* 5–10%, *Lawsonia inermis* 10–15%, *Trigonella foenum-graecum* 5–10%, *Sapinduv mukorossi* 2–5%, *Eclipta alba* 10–15%, a dye of *Acacia catechu* 7–10%, *Emblica officinalis* 10–15%, *Terminalia chebula* 2–4% and *Piper belle* 2–5%.

In one embodiment of the invention, the mordant used is of natural origin and is derived from the above specie.

In another embodiment of the invention, *Juglans regia, Tertninalia chebula, Emblica officinalis, Acacia sinuata, Sapindus mukorossi* are used as fruit extracts and *Indigofera tinctoria, Lawsonia inermis, Trigonella foenum-graecum* and *Piper belle* are used as leaf extracts.

In another embodiment of the invention, the dye of plants is obtained by extraction with water or with an organic solvent such as methanol, ethanol and acetone and mordant.

In yet another embodiment of the invention, the dye used is obtained from plant parts selected from leaves, fruit, rhizomes and root parts.

In another embodiment of the invention, the dye contains tannins and proteins.

The composition causes no hair loss or damage to hair.

In another embodiment of the invention, the composition is nontoxic and safe.

In another embodiment of the invention, no synthetic dye is used.

In another embodiment of the invention, the composition is a non-irritant.

In another embodiment of the invention, the composition provides enhance luster and texture to hair.

In another embodiment of the invention, the composition prevents hair loss and promotes regeneration of hair.

In another embodiment of the invention, the retention time of composition is more in the hair.

In another embodiment of the invention, the composition promotes removal of dandruff.

In another embodiment of the invention, the composition can be used as hair conditioner.

In another embodiment of the invention, the composition can be used for coloring hair.

In another embodiment of the invention, the composition is mixed in water in a ratio of powder to water in the range of 1:20 to 1:25.

In another embodiment of the invention, the composition has pH of from 2 to 5.

In another embodiment of the invention, the composition is used in shoe polishing.

In another embodiment of the invention, the composition is used for shining leather.

In another embodiment of the invention, the composition is used in textile colouring and is non-washable from textiles.

In another embodiment of the invention, the composition is non-sticky to the skin.

In another embodiment of the invention, the composition has no side effects on topical application.

In another embodiment of the invention, the composition is antifungal.

In yet another embodiment of the invention, the composition is anti-allergic.

The present invention provides a method of preparation of a herbal dye composition comprising a mixture of
(a) dyes extracted from plants *Juglans regia, Indigofera tinctoria, Terminalia chebula, Acacia sinuata, Lawsonia inermis, Trigonella foenum-graecum, Sapindus mukorossi Eclipta alba, Embelica officinalis, Acacia catechu* and *Piper belle,*
(b) and a hair color mordant;
the process comprising the steps of;
i. collecting and shade drying plant materials,
ii. powdering dried plant materials to obtain fine/coarse powders,
iii. soaking the powders in a solvent,
iv. concentrating and molding the soaked powder in water mixtures to obtain dyes and mixing the concentrate so obtained with a suitable mordant to obtain the herbal dye composition.

In one embodiment of the invention, component (a) comprises on a wt/wt % of the total composition, a dye of *Juglans regia* 20–30%, a dye of *Indigofera tinctoria* 10–200, a dye of *Acacia sinuata* 5–10%, *Lawsonia inermis* 10–15%, *Trigonella foenum-graecum* 5–10%, *Sapindus mukorossi* 2–5%, *Eclipta alba* 10–15%, a dye of *Acacia catechu* 7–10%, *Emblica officinalis* 10–15%, *Terminalia chebula* 2–4% and *Piper betle* 2–5%.

In another embodiment of the invention, the pH of each of (a) and (b) is in the range of 2 to 5 and the mixture of (a) and (b) has a pH in range of 2 to 5.

In another embodiment of the invention, the composition is mixed in water in a ratio of powder to water in the range of 1:20 to 1:25.

In another embodiment of the invention, the mordant used is of natural origin and is derived from the above specie.

In another embodiment of the invention, *Juglans regia, Terminalia chebula, Emblica officinalis, Acacia sinuata,*

*Sapindus mukorossi* are used as fruit extracts and *Indigofera tinctoria, Lawsonia inermis, Trigonella foenum-graecum* and *Piper betle* are used as leaf extracts.

In another embodiment of the invention, the dyes of plants are obtained by extraction with water or with an organic solvent such as methanol, ethanol and acetone and mordant.

In yet another embodiment of the invention, the dyes are extracted from plant parts selected from leaves, fruit, rhizomes and root parts.

In another embodiment of the invention, the powders are soaked in the solvent for a period of 15–24 hrs and then boiled at a temperature in the range of 85–95° C. for a tie period of 30–50 mutes.

In another embodiment of the invention, the dye contains tannins and proteins.

In another embodiment of the invention, the composition is in the form of a powder, cream, paste, oil or solution.

The present invention also provides a method for coloration of hair using a herbal dye composition comprising a mixture of:
(a) dyes extracted from plants *Juglans regia, Indigofera tinctoria, Terminalia chebula, Acacia sinuata, Lawsonia inermis, Trigonella foenum-graecum, Sapindus mukorossi Eclipta alba, Embelica officinalis, Acacia catechu* and *Piper betle,*
(b) and a hair coloring mordant;
the herbal dye mixture being provided in a single package and applied directly to the hair.

In one embodiment of the invention, the pH of each of (a) and (b) is in the range of 2 to 5 and wherein the combined mixture of (a) and (b) has a pH in range of 3 to 5.

In another embodiment of the invention, the composition is mixed in water in a ratio of powder to water in the range of 1:20 to 1:25.

In another embodiment of the invention, the mordant used is of natural origin and is derived from the above specie.

DETAILED DESCRIPTION OF THE INVENTION

The present invention provides a method of preparing herbal dye from natural dyes and vegetable dyes including from *Juglans regia, Indigofera tinctoria, Terminalia chebula, Acacia sinuata, Lawsonia inermis, Trigonella foenum-graecum, Sapindus mukorossi, Eclipta alba, Embelica officinalis, Acacia catechu* and *Piper betle* dye extracts. The method comprises extracting dyes from the above plants using water and drying the powders from the dye, which can be easily mixed with each other. The black dye prepared in this manner is useful for coloring of hair. The method of obtaining dye from plant material is environmentally friendly since water is used in the extraction.

The subject of the present invention is a hair coloring composition suitable for the coloring of human and animal hair.

*Juglans* Linn is distributed in North and South America and from South Europe to East Asia. Six species are present. *Juglans regia* in the present invention. The rind of unripe wild walnut is used as source material in the method of present invention. It is rich source of proteins.

*Indigofera tinctoria* belongs to genus of leguminous plants originally native to India, China and other tropical subtropical regions. The coloring matter is present in the leaves of the plant in the form of indigotin also known as Indigo blue.

*Eclipta alba* a small genus of herbs is distributed in tropical and subtropical regions of the world. One species occurs in India. The herb is used as tonic and skin diseases. It contains a large amount of resin and alkaloidal principal ecliptine. The herbs also contain poly thienyl compound (alpha—terthienyl methanol) Beta—amyrin and Stigmasterol.

*Acacia catechu* is a tropical tree called Acacia. Brown natural dye obtained chiefly from the wood of *Acacia* water extracts contains mainly catechin. It is a rich source of tannin.

*Emblica officinalis* is indigenous to a large area ranging from the Southern Himalayas of Nepal, North India to South India, Sri Lanka, Burma, Thailand, China and Malaysia. Fruits, barks and leaves are rich source of tannin, Dried pulp of unripe fruits contains 18–30% tannin and at times even more (up to 35%). The fresh fruit is used for cooling, diuretic, laxative and stomachic. The fruit contains phyllemblic acid, lipids, gallic acid and emblical. The seeds also contain fixed oils (Yield 16%).

*Acacia sinuata* is a common, prickly shrub, occurring in tropical jungles throughout India. The pods known as *shikakai*, are extensively used as a detergent. A decoction of the pods relieves biliousness and acts as a purgative. It is used to remove dandruff. An ointment prepared from the ground pods is good for skin diseases. The pods yield saponins (20.6%). The alcoholic extract of the pods on acid hydrolysis gave a sapogenin, acacic acid.

*Lawsonia inermis* is a glabrous, much branched shrub or small tree with grayish brown bark. It is cultivated in many tropical and warm temperature regions. Large scale cultivation for the sake of the leaves which yield the dye, is confined to India, Egypt and Sudan and to some extent, Persia, Madagascar, Pakistan and Australia. Henna has long been used in India and middle East Countries for colouring palms of hands, soles of feet, finger nails and hair. It is harmless and causes no irritation of skin. Alcoholic exacts of henna leaves show mild antibacterial activity. It gave tannin, 10.21%. The tannin content appears to be variable. A sample from Jammu and Kashmir contained 4–5% tannin. The principal colouring matter is lawsone, 2-hydroxy-1:4naphthaquinone which is present in dried leaves. Besides lawsone other constituents present in henna are gallic acid, glucose mannitol, fat resin and traces of an alkaloid.

*Sapindus mukorossi* is a deciduous tree, is native of China, Japan and India and is found in Himalayas from Himachal Pradesh eastwards and in Assam ascending to an altitude of about 1500 m. The tree requires deep well-drained soil for optimum development. Fruits are credited with expectorant and emetic properties and are used in the treatment of excessive salivation, epilepsy and chlorosis. They are also reported to act as fish poison. Powdered seeds are said to possess insecticidal properties. Fruit is valued for the saponin (10%) present in the pericarp which constitutes up to 56.5% of the drupe. A crystalline saponin mukorosside has been isolated from the pericarp. Extract of the pericarp mixed with DDT are used as a fungicide and insecticide.

*Trigonella foenum-graecum* is an aromatic annual 30–60 can in tall, found wild in Kashmir, Punjab and upper Gangetic plains and widely cultivated in many parts of India. Seeds are eaten, boiled or roasted as a vegetable in dyspepsia, diarrhea, dysentery, colic, enlargement of liver and spleen and chronic cough. A paste of the seeds is used as a cosmetic to keep the skin smooth and clean. Seeds contain alkaloid trigonelline, choline, saponin, essential oil, fixed oil, bitter extractive and colouring substance.

*Terminalia chebula* is a large tree found in the sub-Himalayas tract of West Bengal and Assam. It is also found in South India, Sri Lanka, Myanmar and Malaysia. The dried fruits give natural dyes. It is very rich source of tannin (up to 30–35%). Myrobalans are used in fever, cough, asthma, urinary diseases, piles and worms. The fruits contain about 30% of an astringent substance, which is due to characteristic principle chebulinic acid. The fruits also contain tannic acid, gallic acid, resins and some natural anthraquinones.

*Betelvine* (*Piper betle* L) is found in India. Its leaves are used for chewing along with supplements. Betel leaves have many medicinal properties. Its leaves are a source of polyphenols. Fresh juice of betel leaves is used in many *Ayurvedic* preparations.

The present invention is based on the finding of particularly effective method and product for coloring hair. The method and product involve use of dyes and mordants within safe limits. The herbal dye composition of the invention comprises essentially (a) dyes extracted from plants *Juglans regia, Indigofera tinctoria, Terminalia chebula, Acacia sinuata, Lawsonia inermis, Trigonella foenum-graecum, Sapindus mukorossi Eclipta alba, Embelica officinalis, Acacia catechu* and *Piper betle*, and (b) a hair coloring mordant. The pH of each of (a) and (b) is in the range of 2 to 5 and the combined mixture of (a) and (b) has a pH in range of 3 to 5. It is to be understood that the percentage weight of the composition dye components herein are expressed in terms of the total composition.

The black dye obtained in the present invention is useful as a coloring agent for textiles, leather polishing, cosmetics and in beautifying the hair. The ingredients of the dye in terms of wt/wt % are a dye of *Juglan regia* 20–30%, a dye of *Indigofera tinctoria* 10–20%, a dye of *Acacia sinuata* 5–10%, *Lawsonia inermis* 10–15%, *Trigonella foenum-graecum* 5–10%, *Sapindus mukorossi* 2–5%, *Eclipta alba* 10–15%, a dye of *Acacia catechu* 7–10%, *Emblica officinalis* 10–15%, *Terminalia chebula* 24% and *Piper betle* 2–5%.

The mordant used is of natural origin and is derived from the above specie. *Juglans regia, Terminalia chebula, Emblica officinalis, Acacia sinuata, Sapindus mukorossi* are used as fruit extracts ad *Indigofera tinctoria, Lawsonia inermis, Trigonella foenum-graecum* and *Piper betle* are used as leaf extracts. The dye of plants is obtained by extraction with water or with an organic solvent such as methanol, ethanol and acetone and mordant. The dye used may be obtained from plant parts selected from the leaves, fruits, rhizomes and root parts. It is observed that the dye contains tannins and proteins.

The method of preparation of the dye comprises steps of:
i. obtaining the required parts of plants materials and shade drying the material,
v. powdering the dried plant material to obtain a fine/coarse powder,
vi. soaking the materials in a solvent such as water for 15–24 hrs and boiling for a temperature in the range of 85–95° C. for a time period of 30–50 minutes,
vii. exhausting the raw material, concentrating and molding to suitable dye form with suitable mordant under safe limit to obtain the required composition.

The composition is in the form of a powder, cream, paste, oil or solution.

The composition causes no loss or damage to hair. It is observed that the composition is non-toxic and safe, is a non-irritant, provides enhanced luster and texture to hair, prevents hair loss and promotes regeneration of hair. It is also observed that the retention time of composition is more in the hair. The composition also promotes removal of dandruff and can also be used as hair conditioner as well as a hair dye. The composition can be used mixed in water the ratio of powder to water being in the range of 1:20 to 1:25.

The composition of the invention also has several other applications apart from use as a hair dye. It can be used as a shoe polish, for shining leather, for textile coloring. It is particularly observed that the color is fast and is non-washable from textiles.

The composition is also does not stick to the skin and shows no side effects on topical application. The composition also exhibits anti-fungal and anti-allergic properties.

One method of use of the composition comprises providing the hair coloring composition of the invention in a single package for direct application to the hair. No synthetic dye is used in the herbal composition of the invention.

The present invention will now be described with reference to the following illustrative and non-limiting examples.

EXAMPLE 1

*Juglans regia* 20 wt %, *Indigofera tinctoria* 15 wt %, *Eclipta alba* 10 wt %, *Acacia catechu* 7 wt %, *Emblica officinalis* 10 wt %, *Terminalia chebula* 5 wt %, *Piper betle* 3 wt %, *Acacia sinuata* 5 wt %, *Lawsonia inermis* 10 wt %, *Trigonella foenum-graecum* 10 wt % and *Sapindus mukorossi* 5 wt %.

These plant materials were collected, dried in shade till they contain no more than 2–3% water by mass. The shade dried plant materials were crushed to powder form using an electric spreader. The fine powder raw material was soaked in water for 15 hrs. After soaking for 15 hrs it was boiled at simmering point (85–95° C.) for a time period of 30–50 minutes till the dye of raw material is exhausted, to obtain liquid dye. The liquid dye was then concentrated by spray drying to obtain a powder. The plant dye powder was formulated in suitable ratio without mordant to obtain the required composition. This composition was used for hair coloring.

EXAMPLE 2

*Juglans regia* 20 wt %, *Indigofera tinctoria* 10 wt %, *Eclipta alba* 11 wt %, *Acacia catechu* 8 wt %, *Emblica officinalis* 15 wt %, *Terminalia chebula* 3.5 wt %, *Piper betle* 2 wt %, *Acacia sinuata* 10 wt %, *Lawsonia inermis* 10 wt %, *Trigonella foenum-graecum* 5 wt % and *Sapindus mukorossi* 5 wt %. Colouring mordant 0.5 wt %.

The plant materials were collected, dried in shade till they contain no more than 2–3% water by mass. The shade dried plant materials were crushed to powder form using a electric spreader. The fine powdered raw material was soaked in water for 15 hrs. After soaking for 15 hrs it is boiled at simmering point (85–95° C.) for a time period of 30–50 minutes till the dye of raw material is exhausted to obtain liquid dye. This is then concentrated by spray drying to obtain a powder. The plant dye powder was formulated with suitable ratio of a mordant under safe limit to obtain the required composition.

This composition has a synergetic effect on hair. In addition to color the composition increased the luster of hair, did not cause skin irritation and promoted removal of dandruff.

The powder formulation can be packaged and sold commercially for use as herbal black dye for hair or hair colour product.

EXAMPLE 3

*Juglans regia* 25 wt %, *Indigofera tinctoria* 20 wt %, *Eclipta alba* 10 wt %, *Emblica officinalis* 10 wt %, *Terminalia chebula* 8 wt %, *Piper betle* 1.75 wt %, *Acacia sinuata* 5 wt %, *Lawsonia inermis* 15 wt %, *Trigonella foenum-graecum* 5 wt % and colouring mordant 0.25 wt %.

These plant materials were collected and dried in shade till they contain no more than 2–3% water by mass. The shade dried plant materials were crushed to powder form through electric spreader. The fine powder raw material was soaked in water for 15 hrs. After soaking for 15 hrs it was boiled at simmering point (85–95° C.) for a time period of 30–50 minutes till the dye of raw material is exhausted to obtain liquid dye. The liquid dye was concentrated by spray drying to obtain a powder. The plant dye powder was formulated with suitable ratio of mordant under safe limit to obtain the required composition.

The powder dye can be dissolved in hot water at desired ratio. The resulting solution is applied to the hair for 25–30 minute. The solution is then washed away with water.

EXAMPLE 4

*Juglans regia* 30 wt %, *Indigofera tinctoria* 10 wt %, *Eclipta alba* 15wt %, *Emblica officinalis* 10 wt %, *Terminalia chebula* 14.5 wt %, *Lawsonia inermis* 10 wt %, *Trigonella foenum-graecum* 5 wt %, *Sapindus mukorossi* 5 wt % and coloring mordant 0.025 wt %.

These plant materials were collected and dried in shade till they contain no more than 2–3% water by mass. The shade dried plant materials were crushed to powder form using an electric spreader. The fine powder raw material is soaked in water for 15 hrs, After soaking for 15 hrs it is boiled at simmering point (85–95° C.) for a time period of 30–50 minutes till the dye of raw material is exhausted to obtain liquid dye. The liquid dye is diluted in 100 times of volumes of warm water. Benzoic acid was used in dye solution as a preservative.

This liquid dye also is applied in hair colouring.

TABLE 1

| Antifungal activity of herbal black dye | | | |
|---|---|---|---|
| | Herbal Black dye | | Griseofulvin |
| | 2 mg/disc | 4 mg/disc | 25 mg/disc |
| *Candida albicans* | 7 | 10 | 8 |
| *Aspergillus niger* | 6 | 8 | 10 |

Values are inhibition zone (mm)

The composition contains *Juglans regia, Indigofera tinctoria, Eclipta alba, Terminalia chebula, Acacia sinuata, Lawsonia inermis, Trigonella foenum-graecum, Sapindus mukorossi. Embelica officinalis, Acacia catechu* and *Piper betle*, with colour mordant. The results shows better inhibition at 4 mg/disc than that of griseofulvin (25 mg/disc).

Colour Analysis

A microscope chromameter was used with a 0.3 mm diameter. Spot size samples of hair were mounted on 1 cm wide strip of white double-sided sticky tape, which was attached to a microscope slide. The sample positioning stage of the microscope was used to bring the hair fibres into focus and a measurement was taken. The samples (before and after washing) were then randomly repositioned before next measurement and a total of 15 measurements were taken. It was observed that the color of hair was maintained up to one month.

We claim:

1. A herbal dye composition comprising a mixture of:
   (a) dyes extracted from plants *Juglans regia, Indigofera tinctoria, Terminalia chebula, Acacia sinuata, Lawsonia inermis, Trigonella foenum-graecum, Sapindus mukorossi Eclipta alba, Embelica officinalis, Acacia catechu* and *Piper betle,*
   (b) and a hair coloring mordant.

2. A herbal dye composition as claimed in claim 1 wherein the pH of each of (a) and (b) is in the range of 2 to 5.

3. A herbal dye composition as claimed in claim 1 wherein the mixture of (a) and (b) has a pH in range of 2 to 5.

4. A herbal dye composition as claimed in claim 1 wherein component (a) comprises on a wt/wt % of the total composition, a dye of *Juglans regia* 20–30%, a dye of *Indigofera tinctoria* 10–20%, a dye of *Acacia sinuata* 5–10%, *Lawsonia inermis* 10–15%, *Trigonella foenum-graecum* 5–10%, *Sapindus mukorossi* 2–5%, *Eclipta alba* 10–15%, a dye of *Acacia catechu* 7–10%, *Emblica officinalis* 10–15%, *Terminalia chebula* 2–4% and *Piper betle* 2–5%.

5. A herbal dye composition as claimed in claim 1 wherein the mordant used is of natural origin and is derived from the species used for formation of dye.

6. A herbal dye composition as claimed in claim 1 wherein the *Juglans regia, Terminalia chebula, Emblica officinalis, Acacia sinuata, Sapindus mukorossi* are used as fruit extracts.

7. A herbal dye composition as claimed in claim 1 wherein the *Indigofera tinctoria, Lawsonia inermis, Trigonella foenum-graecum* and *Piper betle* are used as leaf extracts.

8. A herbal dye composition as claimed in claim 1 wherein the dye of plants is obtained by extraction with water or with an organic solvent selected from the group consisting of methanol, ethanol and acetone.

9. A herbal dye composition as claimed in claim 1 wherein the dye is obtained from plant parts selected from the group consisting of leaves, fruit, rhizomes and root parts.

10. A herbal dye composition as claimed in claim 1 wherein the dye contains tannins and proteins.

11. A herbal dye composition as claimed in claim 1 wherein the composition causes no hair loss or damage to hair.

12. A herbal dye composition as claimed in claim 1 wherein the composition is nontoxic and safe.

13. A herbal dye composition as claimed in claim 1 wherein no synthetic dye is used.

14. A herbal dye composition as claimed in claim 1 wherein the composition is a non-irritant.

15. A herbal dye composition as claimed in claim 1 wherein the composition provides enhance luster and texture to hair.

16. A herbal dye composition as claimed in claim 1 wherein the composition prevents hair loss and promotes regeneration of hair.

17. A herbal dye composition as claimed in claim 1 wherein the retention time of composition is more in the hair.

18. A herbal dye composition as claimed in claim 1 wherein the composition promotes removal of dandruff.

19. A herbal dye composition as claimed in claim 1 wherein the composition is used as hair conditioner.

20. A herbal dye composition as claimed in claim 1 wherein the composition is mixed in water in a ratio of powder to water in the range of 1:20 to 1:25.

21. A herbal dye composition as claimed in claim 1 wherein the composition is non-sticky to the skin.

22. A herbal dye composition as claimed in claim 1 wherein the composition has no side effects on topical application.

23. A herbal dye composition as claimed in claim 1 wherein the composition is antifungal.

24. A herbal dye composition as claimed in claim 1 wherein the composition is anti-allergic.

25. A method of preparation of a herbal dye composition comprising a mixture of:
   (a) dyes extracted from plants *Juglans regia, Indigofera tinctoria, Terminalia chebula, Acacia sinuata, Lawsonia inermis, Trigonella foenum-graecum, Sapindus mukorossi Eclipta alba, Embelica officinalis, Acacia catechu* and *Piper betle,*
   (b) and a hair coloring mordant;
   the process comprising the steps of:
   i. collecting and shade drying plant materials,
   ii. powdering dried plant materials to obtain fine/coarse powders,
   iii. soaking the powders in a solvent,
   iv. concentrating and molding the soaked powder in water mixtures to obtain dyes and mixing the concentrate so obtained with a suitable mordant to obtain the herbal dye composition.

26. A method as claimed in claim 25 wherein component (a) comprises on a wt/wt % of the total composition, a dye of *Juglans regia* 20–30%, a dye of *Indigofera tinctoria* 10–20%, a dye of *Acacia sinuata* 5–10%, *Lawsonia inermis* 10–15%, *Trigonella foenum-graecum* 5–10%, *Sapindus mukorossi* 2–5%, *Eclipta alba* 10–15%, a dye of *Acacia catechu* 7–10%, *Emblica officinalis* 10–15%, *Terminalia chebula* 2–4% and *Piper belle* 2–5%.

27. A method as claimed in claim 25 wherein the pH of each of (a) and (b) is in the range of 2 to 5 and the mixture of (a) and (b) has a pH in range of 2 to 5.

28. A method as claimed in claim 25 wherein the composition is mixed in water with a powder to water ratio in the range of 1:20 to 1:25.

29. A method as claimed in claim 25 wherein the mordant used is of natural origin and is derived from the plant species of claim 25.

30. A method as claimed in claim 25 wherein the *Juglans regia, Terminalia chebula, Emblica officinalis, Acacia sinuata,* and *Sapindus mukorossi* are used as fruit extracts.

31. A method as claimed in claim 25 wherein the *Indigofera tinctoria, Lawsonia inermis, Trigonella foenum-graecum* and *Piper belle* are used as leaf extracts.

32. A method as claimed in claim 25 wherein the solvent used in step (iii) is selected from water and an organic solvent selected in turn from the group consisting of methanol, ethanol and acetone.

33. A method as claimed in claim 25 wherein the plant materials are selected from the group consisting leaves, fruit, rhizomes and root parts.

34. A method as claimed in claim 25 wherein the powders are soaked in the solvent for a period of 15–24 hrs and then boiled at a temperature in the range of 85–95° C. for a time period of 30–50 minutes.

35. A method as claimed in claim 25 wherein the dye contains tannins and proteins.

36. A method as claimed in claim 25 wherein the composition is in the form of a powder, cream, paste, oil or solution.

37. A method for coloration of hair using a herbal dye composition comprising a mixture of:
   (a) dyes extracted from plants *Juglans regia, Indigofera tinctoria, Terminalia chebula, Acacia sinuata, Lawso-*

*nia inermis, Trigonella foenum-graecum, Sapindus mukorossi Eclipta alba, Embelica officinalis, Acacia catechu* and *Piper belle*, (b) and a hair coloring mordant;

the herbal dye mixture being provided in a single package and applied directly to the hair.

38. A method as claimed in claim 37 wherein the pH of each of (a) and (b) is in the range of 2 to 5 and wherein the combined mixture of (a) and (b) has a pH in range of 3 to 5.

39. A method as claimed in claim 37 wherein the composition is mixed in water in a ratio of powder to water in the range of 1:20 to 1:25.

40. A method as claimed in claim 37 wherein the mordant used is of natural origin and is derived from the plant species of claim 37.

41. A composition as claimed in claim 1 wherein the mordant is *Emblica officinalis* extract.

42. A composition as claimed in claim 1 wherein the *Acacia catechu* is used as binder.

43. A composition as claimed in claim 1 wherein the composition is mixed with a carrier.

44. A composition as claimed in claim 43 wherein the carrier used is distilled water.

* * * * *